United States Patent
Lucente

(10) Patent No.: US 10,948,443 B2
(45) Date of Patent: Mar. 16, 2021

(54) CIGAR MOISTURE METER WITH DIRECT RELATIVE HUMIDITY READOUT

(71) Applicant: Cigarmedics, Inc., Steger, IL (US)

(72) Inventor: Luigi Lucente, Steger, IL (US)

(73) Assignee: Cigarmedics, Inc., Steger, IL (US)

( * ) Notice: Subject to any disclaimer, the term of this patent is extended or adjusted under 35 U.S.C. 154(b) by 0 days.

(21) Appl. No.: 16/435,011

(22) Filed: Jun. 7, 2019

(65) Prior Publication Data

US 2020/0386700 A1  Dec. 10, 2020

(51) Int. Cl.
| G01N 27/04 | (2006.01) |
| G01N 33/00 | (2006.01) |
| G01N 27/12 | (2006.01) |
| A24F 25/00 | (2006.01) |

(52) U.S. Cl.
CPC ......... G01N 27/048 (2013.01); G01N 27/122 (2013.01); G01N 33/0098 (2013.01); *A24F 25/00* (2013.01)

(58) Field of Classification Search
CPC ........ G06F 1/00; G01K 1/00; G01K 2201/00; G01N 1/00; G01N 2201/00
See application file for complete search history.

(56) References Cited

U.S. PATENT DOCUMENTS

| 1,011,763 | A | 12/1911 | Duncan |
| 1,648,655 | A | 11/1927 | Menzies |
| 1,699,090 | A | 1/1929 | Bender |
| 3,319,632 | A | 5/1967 | Burbig |
| 3,732,872 | A | 5/1973 | Lakritz |
| 3,811,087 | A * | 5/1974 | Schmelzer ........... G01N 27/223 324/688 |
| 4,233,995 | A | 11/1980 | Kotuby |
| 4,584,522 | A | 4/1986 | Varela |
| 5,011,009 | A | 4/1991 | Scheurer |
| 5,816,264 | A | 10/1998 | Sebastiani |
| 5,829,452 | A | 11/1998 | Oster |
| 5,957,277 | A | 9/1999 | Elliott |
| 6,604,409 | B1 | 8/2003 | Caldwell |
| 8,069,860 | B2 | 12/2011 | Soyak |
| 9,491,973 | B2 | 11/2016 | Reed |
| 2009/0314300 | A1 | 12/2009 | Cooper |
| 2010/0026300 | A1 * | 2/2010 | Klein ..................... G01N 22/00 324/316 |
| 2014/0002461 | A1 * | 1/2014 | Wang .................... G06F 1/1626 345/440 |
| 2015/0047654 | A1 * | 2/2015 | Thiry ....................... A24C 5/06 131/70 |
| 2015/0197908 | A1 * | 7/2015 | Puppala ............... G01N 27/048 324/696 |
| 2019/0297942 | A1 * | 10/2019 | Kang ...................... A24F 13/24 |

* cited by examiner

*Primary Examiner* — Jermele M Hollington
*Assistant Examiner* — Temilade S Rhodes-Vivour
(74) *Attorney, Agent, or Firm* — Rockman Videbeck & O'Connor

(57) ABSTRACT

A meter includes prongs that detect the moisture content value of a tobacco product, and an electrical circuit of the meter receives this information and converts the moisture content value to a relative humidity value of the tobacco product. The relative humidity value is displayed as a numeral on a display sensor connected to the electrical circuit.

8 Claims, 3 Drawing Sheets

CIGAR MOISTURE METER WITH DIRECT RELATIVE HUMIDITY READOUT

BACKGROUND

1. Field of the Invention

The present disclosure relates to a meter for measuring the moisture content of a cigar, and in particular a moisture content meter that provides a digital readout to the user of the relative humidity of the interior of the cigar.

2. Prior Art

It is well known among cigar smokers that the relative humidity of cigar storage has a direct bearing on the smoker's enjoyment from smoking the cigar. At the retail level, cigars are usually stored and displayed in humidor rooms set at an approximate temperature of 70 degrees Fahrenheit and 70 percent relative humidity. The accepted norm today is to maintain a cigar moisture content in the range of 65-75 percent relative humidity, where the range of a68-72 percent relative humidity is considered optimum. At a relative humidity over 75 percent, mold can grow in the cigar, and the cigar can be difficult to smoke (or draw). When the cigar is kept in relative humidity under 65 percent, it can become hard and dry and the outer wrapper can crack or break.

When a cigar smoker desires to start smoking a cigar, they could be expected to desire information as to the relative humidity of the cigar to ensure that the cigar is suitable to smoke, and will deliver the taste and pleasure the user expects from the smoking experience. There are moisture meters available today that are capable of sensing the moisture content of a cigar prior to use, but those meters do not provide the user with a direct display of the relative humidity of the cigar. Instead these meters display the moisture content, but not in terms of the relative humidity, which is the factor most cigar smokers are used to observing when purchasing and/or using a cigar.

One such moisture content sensing meter is shown in Caldwell, U.S. Pat. No. 6,604,409, where the resistance differential across the probes of the meter in turn indicates the moisture content in the portion of the cigar in contact with the probes after the resistance is amplified by a resistor/transistor coupling prior to being output to the display. The display in the Caldwell patent is shown as a needle indicating "wet," "dry," "good," etc. While the Caldwell patent indicates, but does not illustrate, that a numerical reading could be provided at the display, there is no teaching in the Caldwell patent of a display of relative humidity inside the cigar. Caldwell detects only the moisture content of the cigar, which is a different parameter than relative humidity. Further, the circuit illustrated in Caldwell would not be capable of providing a display of the relative humidity of the cigar being tested.

Therefore, it is an object of the disclosed meter to provide a meter readily usable by a cigar smoker for sensing the moisture content in a cigar and transforming the sensed moisture content into an accurate display of the relative humidity of the cigar about to be smoked stored, or simply used as a diagnostic tool by the cigar industry.

SUMMARY

A cigar moisture meter with electrical probes connected to a circuit that transforms a reading of resistance across the probes of the meter into a visual display of the relative humidity inside the cigar. The meter's circuit receives the resistance reading of the moisture content of the cigar, and using a preinstalled table comprising values of relative humidity for moisture content at a given temperature converts the moisture content value to a relative humidity value. The relative humidity value is then electronically displayed on a screen visible to a user.

These and other aspects of the present disclosure are disclosed in the following detailed description of the embodiments, the appended claims and the accompanying figures.

BRIEF DESCRIPTION OF THE DRAWINGS

The various features, advantages, and other uses of the apparatus will become more apparent by referring to the following detailed description and drawings, wherein like reference numerals refer to like parts throughout the several views. It is emphasized that, according to common practice, the various features of the drawings are not to-scale. On the contrary, the dimensions of the various features are arbitrarily expanded or reduced for clarity.

FIGS. 7 and 7A-7F comprise schematic portions of the electronic circuit elements for operating the meter of the present invention.

DETAILED DESCRIPTION

Figure 4:
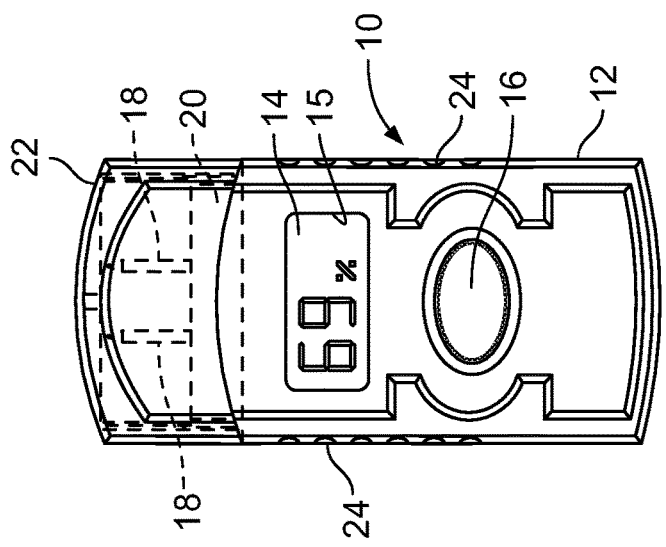
FIG. 4 is a front elevation view of the meter of FIG. 1 with the protective cap in place over the prongs of the meter.

Referring to FIGS. 1-4 of the drawings, which illustrate one embodiment of the presently disclosed cigar moisture meter 10, the meter 10 has a casing 12 made of plastic or some other suitable material, with a chamber (not shown) on the interior of casing 12. The front of the casing 12 includes a lighted digital display 14 and an activation and deactivation button 16. Digital display 14 can be visible through an aperture 15 formed in casing 12, or display 14 can be mounted on an outer surface of casing 12. A pair of electrically conductive pointed prongs 18 extend from the top 20 of casing 12. The other end of each prong 18 is connected to the electronic circuit shown in FIG. 7. A protective cap 22 is removably and frictionally attached to the side walls of top 20 of casing 12, with the pointed ends of prongs 18 concealed under cap 22 when the cap is inserted on top of casing 12, as shown in FIG. 4. The sides of casing 12 include notches 24 for ease of gripping by a user.

Figure 1:
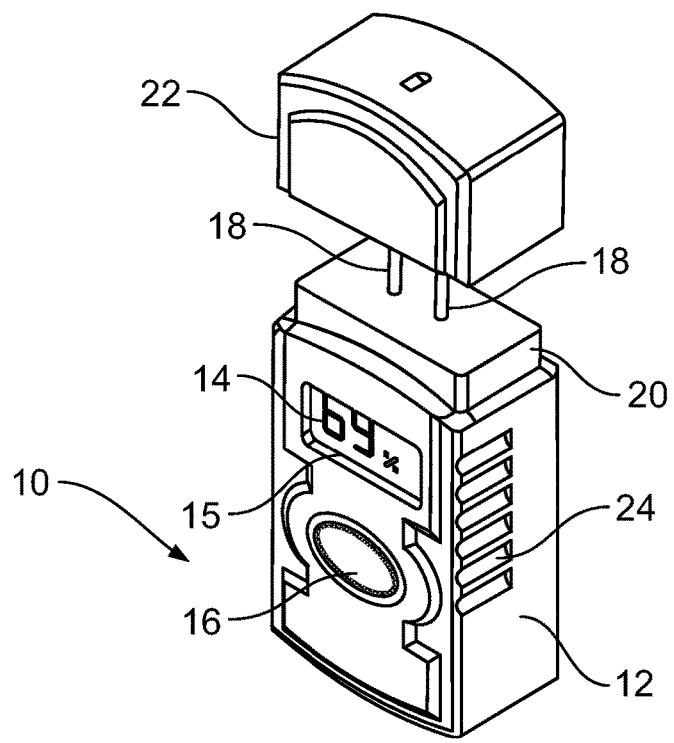
FIG. 1 is a front side perspective view of the meter of the present disclosure, with the protective cap removed.
Figure 2:
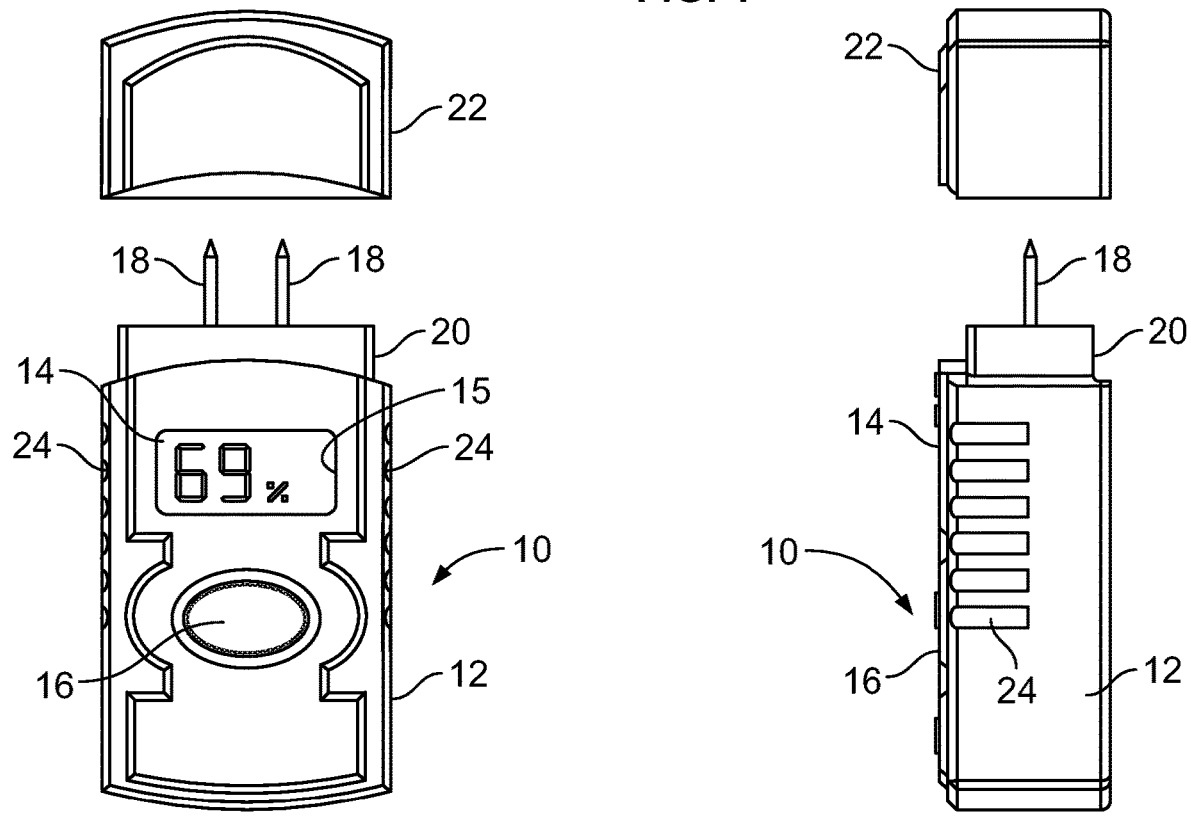
FIG. 2 is a front elevation view of the meter of FIG. 1 with the protective cap removed.
Figure 3:
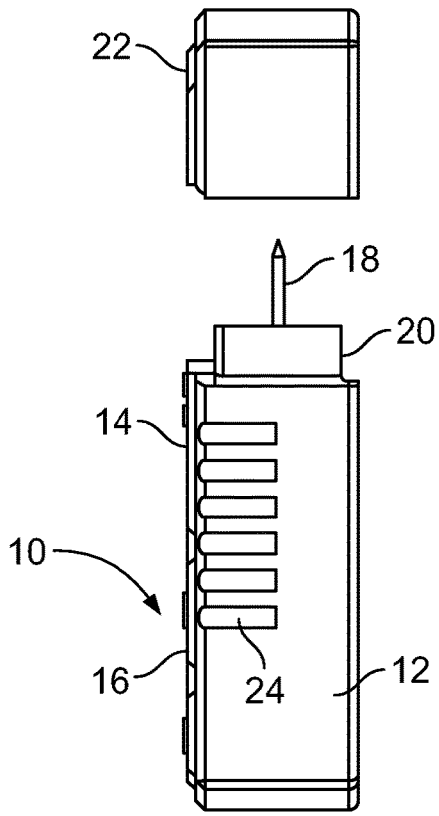
FIG. 3 is a side elevation view of the meter of FIG. 1 with the protective cap removed.
Figure 5:
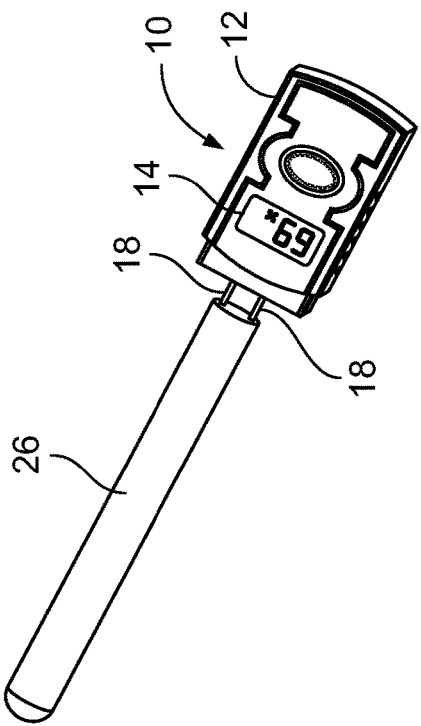
FIG. 5 is a perspective view of the meter of FIG. 1 with the prongs inserted into an end of a cigar.
Figure 6:
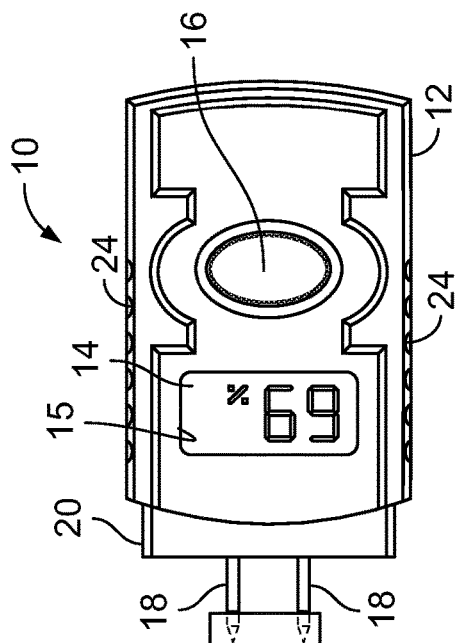
FIG. 6 is a front elevation view of the meter of FIG. 1 with the prongs inserted into an end of a cigar.

FIGS. 5 and 6 illustrate the prongs 18 of meter 10 inserted into an end of cigar 26. The moisture content in the cigar creates an electrical resistance value between prongs 18, and the electrical resistance value is conveyed to electronic circuit 30 shown in FIG. 7, as will be explained.

Figure 7:
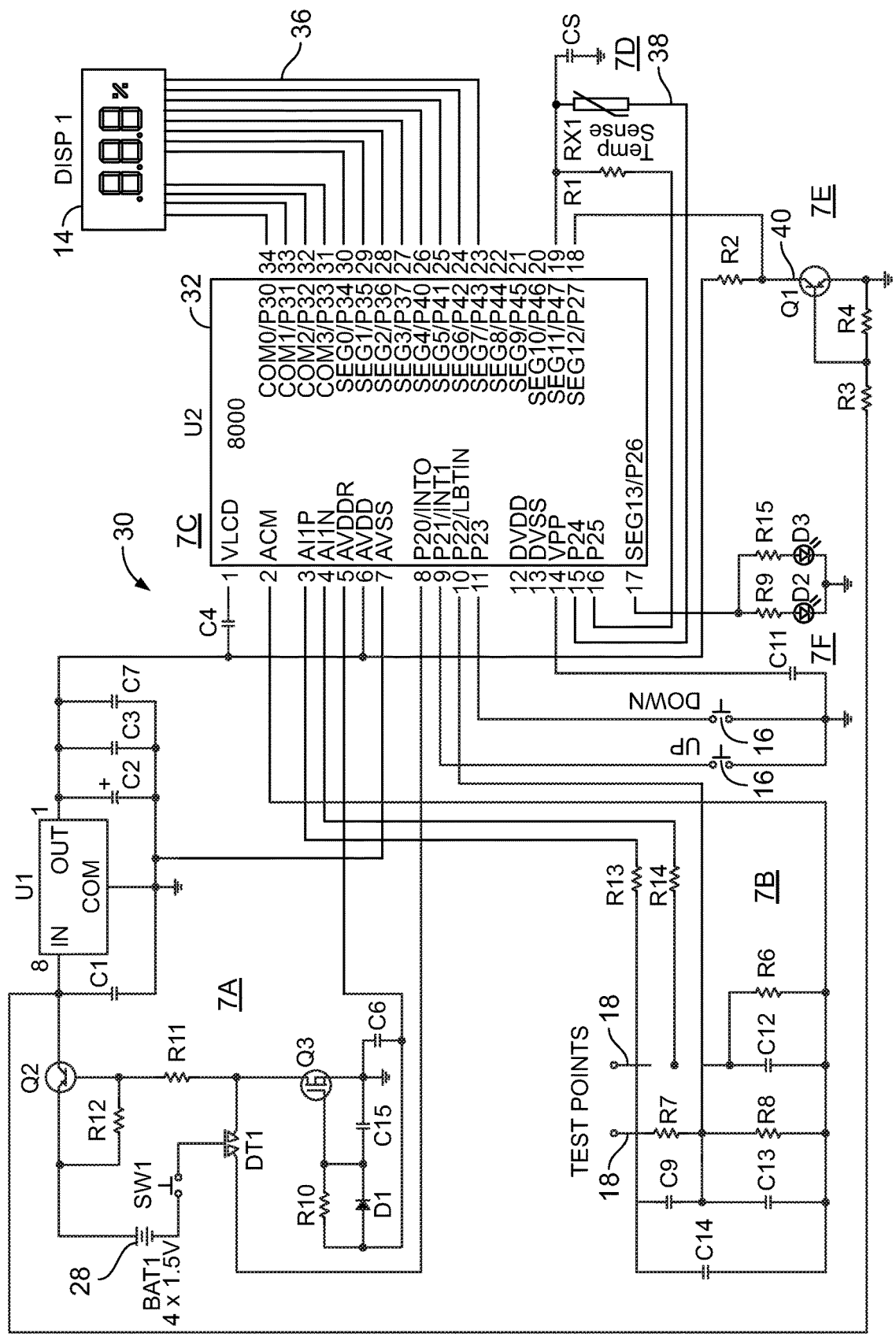

Referring to FIG. 7, electronic circuit 30 comprises a power supply subcircuit 7A, a resistance subcircuit 7B connected to contacts 18, a main subcircuit 7C including a microprocessor 32, a temperature sensing subcircuit 7D and a low battery subcircuit 7E, and a switch circuit 7F.

The power supply output (FIG. 7A) is connected to microprocessor 32 (FIG. 7C). Microprocessor 32 is also electronically connected to prongs 18 (FIG. 1) of the resistance circuit shown at FIG. 7B. Electrical conductors 36 connect display 14 to microprocessor 32.

A thermistor or temperature sensor 38 subcircuit. FIG. 7D is connected to microprocessor 32. Sensor 38 provides a signal responsive to the temperature of the cigar material 26. The temperature signal is then conveyed to microprocessor 32. Microprocessor 32 also receives the signal from prongs 18 reflecting the moisture content of the tobacco in the cigar 26.

Microprocessor 32 includes embedded data comprising relationships of relative humidity values for given increments of moisture content of cigar 26 at multiple temperatures. When a moisture content value signal is generated at prongs 18 (FIG. 7B), the signal is transmitted to microprocessor 32, and is converted to a relative humidity value for the temperature sensed by thermistor 38. The converted relative humidity value is conveyed to connectors 36, and a readable numeral designating the relative humidity percentage value appears on display 14.

A low battery circuit 40 (FIG. 7E) provides a visual signal advising the user that power source 28 needs to be recharged or replaced.

In an alternate embodiment of the presently disclosed relative humidity meter, microprocessor 32 includes data for converting moisture content information to a relative humidity value at a single given temperature. For example, the given temperature may be 70 degrees F., which is the temperature cigars are normally stored in humidors.

The prongs 18 can also be used as a small hole insert or punch to cut two small holes in the cap of the cigar to allow ease of draw.

The meter 10 described above can be used to read the moisture content and display the relative humidity factor of cigars, cigarillos, cigarette tobacco, chewing tobacco, snuff, hookah material, pipe tobacco, and medicinal marijuana.

While the present disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A meter for detecting the moisture content of a tobacco product and displaying the relative humidity of the tobacco product, comprising:
    a casing forming an interior chamber of the casing;
    a pair of prongs extending outwardly from the casing;
    an electronic measuring circuit disposed in the interior chamber, the electronic circuit including a power source;
    the electronic measuring circuit including an electronic display screen;
    the electronic display screen and the pair of prongs electrically connected to the electronic measuring circuit;
    the pair of prongs adapted to be inserted into the tobacco product and generate an electrical signal reflecting a tobacco product moisture content value across the pair of prongs;
    the electrical signal reflecting the tobacco product moisture content value transmitted to the electronic measuring circuit;
    the electronic measuring circuit converting the tobacco product moisture content value signal to a signal reflective of a relative humidity value of the tobacco product;
    the electronic measuring circuit displaying a numerical designation of the relative humidity of the tobacco product on the electronic display screen.

2. The meter of claim 1 wherein:
    the electronic measuring circuit includes a temperature sensor adapted to sense the temperature of the tobacco product;
    the electronic measuring circuit converting the tobacco product moisture content value signal to a signal reflective of the relative humidity value of the tobacco product at a specified temperature of the tobacco product.

3. The meter of claim 1, wherein:
    the electronic display screen is disposed on an outer surface of the casing.

4. The meter of claim 1, wherein:
    the electronic display screen is visible through an aperture of the casing.

5. The meter of claim 1, wherein:
    the electronic measuring circuit is adapted to measure the electrical resistance of the moisture content of the tobacco product across the pair of prongs.

6. The method of detecting the moisture content of a tobacco product and displaying a numerical representation on an electronic display screen of a meter, the numerical representation displaying the relative humidity value of the tobacco product, comprising the steps of:
    obtaining a measurement of a tobacco product moisture content value;
    electronically converting the tobacco product moisture content value measurement to a relative humidity value for the tobacco product; and
    displaying a numerical representation of the relative humidity value of the tobacco product on the electronic display screen.

7. The method of claim 6, further including the steps of:
    determining the tobacco product moisture content value at the extant temperature of the tobacco product;
    determining the relative humidity value of the tobacco product at the extant temperature;
    electronically converting the tobacco product moisture content value to a relative humidity value; and
    displaying the relative humidity value on the electronic display screen.

8. The method of claim 6 wherein:
    the step of obtaining a measurement of the tobacco product moisture content wherein a pair of prongs extend outwardly from the meter, including the step of inserting the pair of prongs into an end of the tobacco product and forming a pair of holes in the end of the tobacco product.

* * * * *